United States Patent
Jaworowski et al.

[11] Patent Number: 6,165,542
[45] Date of Patent: Dec. 26, 2000

[54] METHOD FOR FABRICATING AND INSPECTING COATINGS

[75] Inventors: Mark Jaworowski, Glastonbury; Glenn T. Janowsky, Coventry; Charles H. Weston, Salem, all of Conn.

[73] Assignee: United Technologies Corporation, Hartford, Conn.

[21] Appl. No.: 09/220,545

[22] Filed: Dec. 23, 1998

[51] Int. Cl.[7] ................................................. B05D 1/12
[52] U.S. Cl. .............................. 427/10; 427/9; 427/455; 427/456; 427/425
[58] Field of Search ........................... 427/8, 9, 10, 455, 427/456, 424, 422, 425

[56] References Cited

U.S. PATENT DOCUMENTS

| | | |
|---|---|---|
| 3,655,907 | 4/1972 | Philibert et al. . |
| 3,737,764 | 6/1973 | Dufayet . |
| 3,790,198 | 2/1974 | Hagen . |
| 4,312,748 | 1/1982 | Rozmus . |
| 4,564,810 | 1/1986 | Geithman et al. . |
| 4,603,257 | 7/1986 | Packer et al. . |
| 4,608,534 | 8/1986 | Cecco et al. . |
| 4,613,259 | 9/1986 | Packer et al. . |
| 4,634,462 | 1/1987 | Fish et al. . |
| 4,712,074 | 12/1987 | Harvey . |
| 4,742,299 | 5/1988 | Stone . |
| 4,783,341 | 11/1988 | Packer et al. . |
| 4,893,079 | 1/1990 | Kustra et al. . |
| 4,897,605 | 1/1990 | Cox et al. . |
| 5,057,659 | 10/1991 | Schneider et al. . |
| 5,136,497 | 8/1992 | Coe et al. . |
| 5,202,837 | 4/1993 | Coe et al. . |
| 5,239,864 | 3/1993 | von Pragenau . |
| 5,294,765 | 3/1994 | Archibald et al. . |
| 5,327,081 | 7/1994 | Rudd et al. . |
| 5,343,146 | 8/1994 | Koch et al. . |
| 5,345,514 | 9/1994 | Mahdavieh et al. . |
| 5,365,663 | 11/1994 | Demartini . |
| 5,420,518 | 5/1995 | Schafer, Jr. . |
| 5,423,222 | 6/1995 | Rudd et al. . |
| 5,430,376 | 7/1995 | Viertl . |
| 5,433,654 | 7/1995 | Clark, Jr. et al. . |
| 5,481,916 | 1/1996 | Macecek et al. . |
| 5,532,589 | 7/1996 | Gammell . |
| 5,536,022 | 7/1996 | Sileo et al. . |
| 5,548,213 | 8/1996 | Kohmura et al. ........................ 324/232 |
| 5,569,363 | 10/1996 | Bayer et al. . |
| 5,623,427 | 4/1997 | Vandervalk et al. . |
| 5,640,019 | 6/1997 | Ehemann, Jr. et al. . |
| 5,721,057 | 2/1998 | Bamberg et al. . |

(List continued on next page.)

FOREIGN PATENT DOCUMENTS 783371 12/1980 U.S.S.R. .

OTHER PUBLICATIONS

Fanelli et al., "Prediction of Strength of Graphitic Material by Nondestructive Test Techniques", *American Society for Testing and Materials Special Technical Publication No. 439*, 1968 Pennsylvania, pp. 48–60.

(List continued on next page.)

*Primary Examiner*—Shrive Beck
*Assistant Examiner*—Paul D. Strain

[57] ABSTRACT

A method of fabrication and inspection includes depositing a coating and determining at least one physical property of the coating using eddy current techniques. In a detailed embodiment an abradable coating having a metal volume fraction in the range of from 0.3 to 0.5 is applied to an inner circumference of a stator for a gas turbine engine compressor. The eddy current probe is positioned by a manipulator. A distance separating the probe and a surface of the coating is measured using a frequency above one megahertz (MHz). The thickness of the coating is measured by determining the rolloff frequency for the coating's complex impedance. The coating density is determined by its complex impedance at a characteristic frequency below four MHz. The density can be used as an indication of the performance of the coating with respect to abradability and the erosion resistance. The measurements may also be applied as a post-process quality control technique.

24 Claims, 3 Drawing Sheets

U.S. PATENT DOCUMENTS

| | | |
|---|---|---|
| 5,760,573 | 6/1998 | Paranjpe et al. . |
| 5,780,116 | 7/1998 | Sileo et al. ............................. 427/456 |
| 5,780,146 | 7/1998 | Mason et al. . |
| 5,781,007 | 7/1998 | Partika et al. . |
| 5,791,871 | 8/1998 | Sech et al. . |
| 5,798,439 | 8/1998 | Lefebvre et al. . |
| 5,879,753 | 3/1999 | Zajchowski et al. .................. 427/454 |

OTHER PUBLICATIONS

McClung, R.W., "Nondestructive Testing of Nuclear Ceramic Materials", *American Ceramic Society*, BUULL V//4//9N/9, Sep. 1970 Tennessee, pp. 777–781.

Slyusarev et al., "Non–Contact Electromagnetic Converter for Mechanical Displacement Transformation into Electric Signals", *Latvijas PSR Zinatnu Akademijas Vestis, Fizikas un Tehnisko Zinatnu Serija*, No. 4, 1973 USSR, pp. 103–109.

Bushnell et al, "Correlation of NDT and Mechanical Properties", ITT Research Institute, Proceedings of the Conference, Chicago, IL, Oct. 15–17, 1974 Illinois, pp. 209–221.

May, James, "Eddy Current and Coercive Force Measurements for Evaluation of Sintered Carbide Cutting Tools", *Materials Evaluation*, vol. 33, No. 8, Aug. 1975 Michigan, pp. 200–202.

Henstock, Michael, "Modern Techniques for Recycling", *Conservation & Recycling*, vol. 1, 1976 Great Britain, pp. 83–90.

Morgan et al., "Equipment for Nondestructive Evaluation of the Strength of the Fort St. Vrain Core–Support Blocks", Prepared by Pacific Northwest Laboratory for DOE, PNL–4480, Sep. 1982 USA.

Morgan et al., "Feasibility of Monitoring the Strength of HTGR Core Support Graphite—Part III", Prepared by Pacific Northwest Laboratory for NRC, NUREG/CR–2929; PNL–4449, Feb. 1983 USA.

Zinchenko et al., "Effect of Molding Pressure on the System of Physicomechanical Characteristics of a Carbon Fiber Reinforced Plastic (FRP)", *Mechanics of Composite Materials*, vol. 19, No. 1, Jan.–Feb. 1983 USA, pp. 85–88.

Kuz'min, V.S., "Galvanomagnetic Effects in Uncompensated Metals in Non–Uniform Magnetic Fields", *Dokl. Akad. Nauk BSSR*, vol. 28, No. 6, 1984 Russia, pp. 523–526.

Copley et al., "Nondestructive Evaluation of Carbon–Carbon Coatings", Prepared by General Electric Co. for Air Force Wright Aeronautical Labs, AFWAL–TR–87–4086, Oct. 1987 USA.

Wadley et al., "Eddy Current Measurement of Density During Hot Isostatic Pressing", *Review of Progress in Quantitative Nondestructive Evaluation*, vol. 7B, 1988 USA, pp. 1589–1598.

Zinchenko et al., "Determination of Density of Carbon Plastics by Eddy Current Testing", *Mekh. Kompoz. Material*, (5), Sep.–Oct. 1989 Russia, pp. 927–930.

Feickert, C.A., "Selective Screening of High Temperature Superconductors by Resonant Eddy Current Analysis" *USACERLTechnical Report M 91/09* Nov. 1990 USA.

Liaw et al., "Process–Interactive Nondestructive Evaluation for Metal–Matrix Composites", Conference paper published by The Minerals, Metals & Materials Society, 1991 Pennsylvania, pp. 193–208.

Sweet et al., "Control of Sintered Density in Copper Compacts", *Sintering Advances in Powder Metallurgy*, vol. 4 1991 New Jersey, pp. 87–102.

Higuchi et al., "Effect of Nodular Corrosion Density on Thickness Measurement by Eddy–Current Technique", *Fuel 90's*, vol. 2 1991 Illinois, pp. 749–756.

Liaw et al., "Nondestructive Characterization for Metal–Matrix Composite Fabrication", *American Society for Testing and Materials Special Technical Publication No. 1157* 1992 Pennsylvania, pp. 251–277.

Liaw et al. "Determining Material Properties of Metal–Matrix Composites by NDE", *JOM* vol. 44, No. 10 Oct. 1992 USA, pp. 36–40.

Burke et al., "Nondestructive Characterization of Advanced Composite Materials", *Materials Forum*, vol. 18 1994 USA, pp. 85–109.

Dharmasena et al., Eddy Current Techniques for Density Measurements During Hot Isostatic Pressing of Titanimum Matrix Composites, *Nippon Kinzoku Gakkai Koen Gaiyo*, vol. 117 1995 Japan, p. 199.

Miyazawa et al., "Monitoring of Metal Powder–Binder Mixing Process by Eddy–Current Sensor", *Journal of Materials Processing Technology*, vol. 48, No. 1–4 Jan. 1995 USA, pp. 765–770.

Johnson, Duane P., "Nondestructive Flaw Detection and Density Measurements in Powder Metallurgy Parts SBIR Phase I", *Advances in Powder Metallurgy and Particulate Materials*, vol. 3 1995 New Jersey, pp. 9/17–9/30.

Johnson, Duane P., "Nondestructive Flaw Detection and Density Measurements in Powder Metallurgy Parts—Part I", *Industrial Heating*, vol. 63, No. 6, Jun. 1996 USA, pp. 45–47.

Johnson, Duane P., "Nondestructive Flaw Detection and Density Measurements in Powder Metallurgy Parts—Part II", *Industrial Heating*, vol. 63, No. 8, Aug. 1996 USA, pp. 41–45.

Kunze et al., "The Densification of Metal Coated Fibers: Hot Isostatic Pressing Experiments", *Acta Materialia*, vol. 45, No. 5, May 1997 Great Britain, pp. 1851–1865.

Miyazawa et al., "Monitoring of Metal–Powder Diameter by Eddy–Current Sensor", *Journal of Materials Processing Technology*, vol. 63, No. 1–3, Jan. 1997 USA, pp. 303–306.

METHOD FOR FABRICATING AND INSPECTING COATINGS

TECHNICAL FIELD

The invention relates to a method for fabricating and inspecting coatings, more particularly to a method for fabricating and inspecting coatings that employs eddy current techniques to determine a physical property of the coating.

BACKGROUND ART

A gas turbine engine employs various coatings. Some of these coatings comprise a metal and a non metal, or a metal and intentional porosity, deposited on a metal substrate by thermal spray methods. These coatings typically have a low metal volume fraction, typically in the range of from 0.3 to 0.5, compared to that of solid metal. The coating service performance can often be predicted on the basis of one or more properties of the coatings. The performance of the coatings often has an effect on the performance of the gas turbine engine. Thus, it is desirable to be able to determine various properties of the coatings.

For example, thermal sprayed coatings are commonly used in gas turbine engines and other types of turbomachinery. The thermal spray process is capable of depositing coatings containing a wide range of metallic, ceramic and polymeric constituents. The composition of these coatings can be adjusted to provide a combination of properties, i.e., erosion resistance and abradability, that allow the coatings to deliver superior performance as compressor outer air seals.

U.S. Pat. No. 4,783,341 to Packer et al. discloses a method for making and inspecting porous metal plasma sprayed abradable seals. Radiation transmission techniques are utilized to determine the as-sprayed density of a deposit containing metal and polymer powder particles. Based on the measuring density, a mathematical prediction is made of what the surface hardness of the sprayed deposit will be after it has been machined and then heated to remove the polymer powder particles. However, this method requires the use of radioactive material.

U.S. Pat. No. 5,202,837 to Cos et al discloses that eddy current techniques can be used to track density, shape, and grain size of material during consolidation processes. However, the relative densities monitored range from an ideal of 1.0 to a low of only 0.6. Furthermore, unlike an abradable seal having a low metal volume fraction of 0.3 to 0.5, such processes typically results in a relatively uniform microstructure with few pores due to the high relative density.

DISCLOSURE OF THE INVENTION

An object of the present invention is to provide a method for non destructively determining one or more properties of a coating having a metal volume fraction of no greater than 0.5, without the need for a radioactive source.

According to a first aspect of the present invention, a method for inspecting a non homogenous coating with a metal volume fraction of no greater than 0.5 includes using eddy current techniques to determine at least one physical property of the coating, wherein the at least one physical property has been correlated to performance of the coating.

According to a second aspect of the present invention, a method of fabricating an annular component having a coating with a relative density of no greater than 0.5 thereon and for measuring at least one physical property of the coating, comprising the steps of rotating the component relative to a sprayed stream of metal particles and other particles having low conductivity relative to that of the metal particles, wherein the metal and the other particles are deposited onto the surface of the component, and determining at least one physical property of the coating using eddy current techniques.

The present invention enables properties of a coating having a metal volume fraction of no greater than 0.5 to be determined without the need for a radioactive source. In a detailed embodiment, a thickness and a density of the coating are determined. The distance separating the probe and a surface of the coating is measured using a frequency above one megahertz (MHz) that is unaffected by the density of the coating. The thickness of the coating is measured by determining the rolloff frequency for the coating's complex impedance. The coating density is determined by its complex impedance at a characteristic frequency below four MHz. The density can be used as an indication of the performance of the coating with respect to abradability and the erosion resistance. The measurements may be applied during the thermal spray process to dynamically control the density of the abradable coating as it is deposited. The measurements may also be applied as a post-process quality control technique.

These and other objects, features and advantages of the present invention will become more apparent in the light of the following detailed description, accompanying drawings, and claims.

BEST MODE EMBODIMENT FOR CARRYING OUT THE INVENTION

Figure 1:
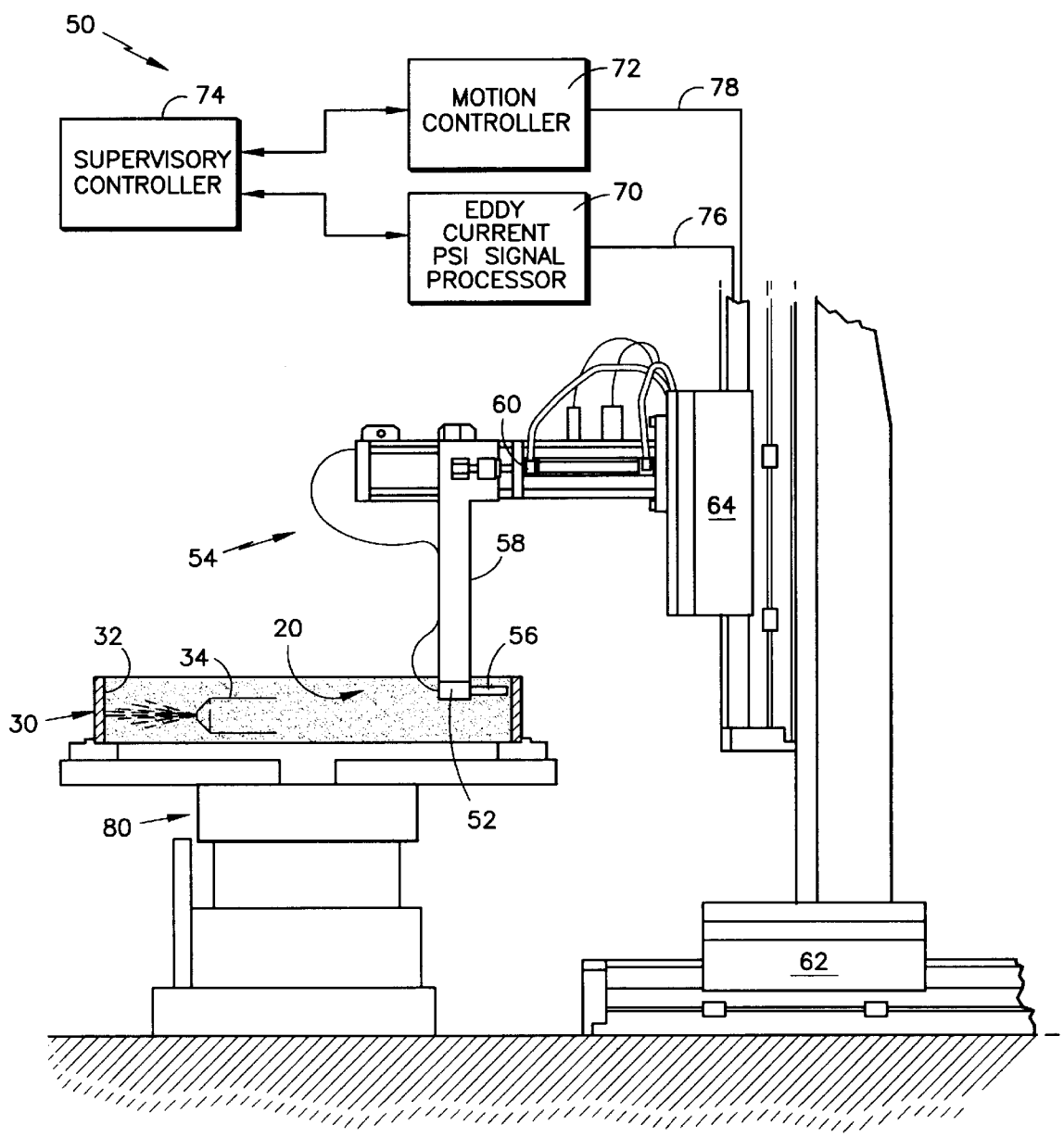
FIG. 1 is a schematic representation of a system for fabricating and inspecting an abradable seal for a gas turbine engine.

The present invention is disclosed with respect to a best mode embodiment for use in fabricating and inspecting a coating that serves as an abradable seal 20 on a stator 30 as illustrated in FIG. 1. Referring now to FIG. 1, an abradable seal is deposited on an inner surface of an inner wall 32 of the stator 30 by a thermal spray system, represented in part by a nozzle 34. The abradable seal serves as an outer air seal (OAS) in a gas turbine engine, to reduce clearances between the stator 30 and rotating blades (not shown). As the abradable seal is deposited, relative rotation is provided between the stator 30 and the thermal spray system 34. The rotational speed may be about sixty revolutions per minute. The thermal spray system 34 deposits the abradable seal 20 as a mixture. The mixture may comprise a metal and either polymer or ceramic powders. The metal is typically a superalloy or a refractorymodified MCrAly, where M is nickel, cobalt, iron, or a mixture of these elements. The polymer powder is typically a decomposable organic material such as polyester or polymethyl ethacrylate. The preferred ceramic powder is BN (boron nitride). A thin bond coating (not shown) is applied to the inner surface of the inner wall 34 of the stator 30 to enhance the adhesion of the abradable seal. The bond coating is typically a refractory modified MCrAly.

The thickness of the abradable seal 20 typically increases at a rate of 0.001 to 0.002 inches per minute during deposition. Upon completion of the deposition, the abradable seal 20 typically has an as deposited thickness in a range of from 0.100 inches to 0.150 inches. The abradable seal 20 is then typically machined to a thickness in a range of from 0.040 inches to 0.100 inches, e.g., 0.050 inches. It should be understood that the thickness of abradable seals is not limited to the ranges described above. U.S. Pat. No. 5,780,116 discloses a method for producing an abradable seal and is incorporated by reference herein.

Figure 2A:
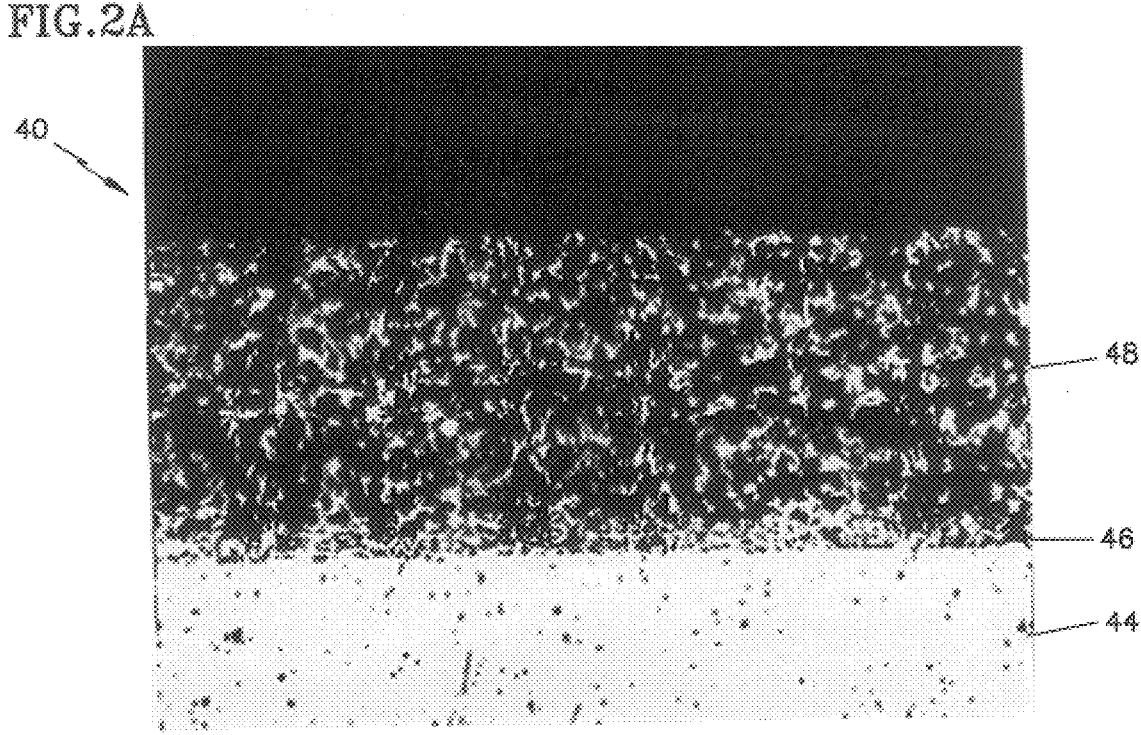
FIG. 2A is a photomicrograph of a gas turbine engine abradable seal on a metal substrate.
Figure 2B:
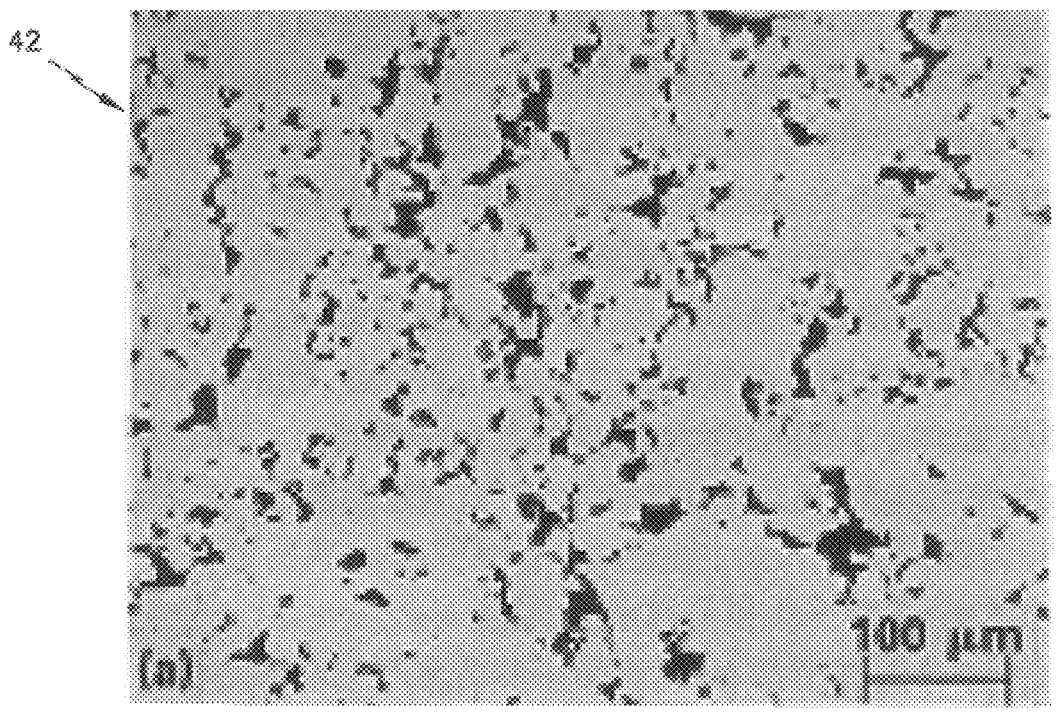
FIG. 2B is a photomicrograph of a powder metal part after sintering.

FIGS. 2A and 2B are a photomicrograph 40 of a typical gas turbine engine abradable seal on a metal substrate and a photomicrograph 42 of a sintered powder metal component, respectively. Referring now to FIG. 2A, the photomicrograph 40 illustrates a metal substrate 44, a thin bond coating 46, and an abradable seal 48. The metal substrate 44 has a high metal volume fraction. The abradable seal 48 has a relatively low metal volume fraction, in the range of from 0.3 to 0.5, and usually has a microstructure characterized by fused metal particles and pockets of non metal material. In contrast, the photomicrograph 40 (FIG. 2B) of the sintered powder metal component illustrates that the sintered powder metal component has a high relative density.

It is known that the performance of the seal 20 is related to its abradability and its erosion resistance. It is also known that the abradability and the erosion resistance can be predicted on the basis of the density of the seal. This is because the density of the seal is an indicator of the ratio of the amount of the metal and nonmetal components in the seal.

A measurement system 50 is provided in order to measure the thickness and the density of the abradable seal 20, as described hereinbelow. The measurement system 50 includes a sensor head 52 and a manipulator 54. The sensor head 52 includes an eddy current probe 56. The eddy current probe 56 may be of a differential type such as for example a Model # 220072 manufactured by Centurion Inc. The eddy current probe 56 is spaced apart from the stator/seal by a distance. The sensor head 52 may further include features such as "swing away" bracketing, EMI-shielded cabling, water cooling and compressed air cleaning to provide ease of use and measurement stability in the thermal spray environment. The sensor head 52 is attached to the manipulator 54 by way of bracket assembly 58. The manipulator 54 may include a pneumatic slide 60 and x- and y-axis linear slides 62, 64 that provide movement to position the sensor head 52 with respect to the surface of the abradable seal 20. The pneumatic slide 60 provides an additional degree of freedom for the head 52 to clear obstructions on the stator 30 (flanges, vanes, etc.) to gain access to the seal pocket area. This has the additional benefit of reducing the amount of travel needed for the x-axis linear slide 62, and therefore the footprint of the device. In an alternative embodiment, the eddy current probe may be incorporated into the production fixturing.

The measurement system 50 may further include an eddy current power supply/signal processor 70, a motion controller 72, and a supervisory controller 74. The eddy current power supply/signal processor 70 is electrically connected to the eddy current probe 56 via power supply and return signal lines, represented by a signal line 76, to define an eddy current measurement system. The motion controller 72 is electrically connected to the manipulator 54 and the rotary table via power supply and control lines, again represented by a signal line 78. The motion controller 72 directs the movement of the manipulator 54. The supervisory controller 74, which may be a PC, provides positioning commands to the motion controller 72 and measurement commands to the eddy current signal processor 70. The supervisor controller in turn receives data signals from the eddy current signal processor 70 and the motion controller 72.

In operation of the eddy current measurement system, the eddy current signal processor 70 provides a drive signal to the eddy current probe 56. The drive signal causes the eddy current probe 56 to generate a time varying electromagnetic field, which induces an eddy current in the abradable seal 20. The eddy current probe 56 senses the eddy current and generates a measurement signal indicative thereof The eddy current probe 56 provides the measurement signal to the eddy current signal processor 70, which provides signal conditioning and generates a data signal indicative of an electrical voltage, which is in turn indicative of an electrical impedance of the seal. The electrical impedance typically depends on the frequency of the drive signal, which in turn determines the frequency of the electromagnetic field. The electrical impedance (Z) has a real component (R) and a reactive component (X), and is computed in accordance with equations (1) and (2):

$$Z = \sqrt{R^2 + X_L^2} \qquad (eq.\ 1)$$

$$\angle Z = \tan^{-1}(X_L/R) \qquad (eq.\ 2)$$

The measurement system 50 may make repeated measurements of the thickness and the density as the stator 30 is rotated during deposition of the bond coating and the abradable seal 20. In making these measurements, the measurement system 50 is also used to determine the distance between the eddy current probe 56 and the seal/stator. The distance between the probe 56 and stator 30 may need to be determined at multiple points along the circumference of the seal to account for any out of roundness of the stator 30. Measurement of the thickness and the density is carried out as a series of operations including 1) measurement and adjustment of the probe to seal distance, 2) thickness measurement and 3) density measurement, referred to herein as a measurement cycle.

Upon initial placement of the stator 30 on the rotary table 80, the supervisory controller 74 determines the location of the seal surface and the probe to seal distance. This is accomplished by using the pneumatic slide and the x-axis linear slide to bring the eddy current probe 56 into close proximity to the seal surface. The probe to seal distance is measured, as described hereinbelow, and adjusted by the supervisory controller 74 to a satisfactory value such as 0.250" from the seal surface. The stator 30 may be indexed through a rotation of 360 degrees to verify that the measured probe to seal distance is correct and that the stator 30 is adequately round.

The measurement of the probe to seal distance is accomplished by operating the eddy current measurement system with a drive signal of a high frequency. The frequency is preferably in the range of one megahertz (MHz) to ten MHz, more preferably four MHz or greater. Because of the high frequency of the drive signal, the electromagnetic field from the eddy current probe 56 has a high frequency and does not significantly penetrate the seal surface. As such, eddy currents induced in the seal do not penetrate deeply into the seal, and the eddy current measurement system functions as a distance sensor, i.e., the response of the eddy current measurement signal is a function of the probe to seal distance. This distance is determined on the basis of the resulting impedance in combination with a calibration formula or a data table indicative of a calibration curve. After the probe to seal distance has been measured, it may be adjusted using the manipulator 54 as needed to maintain a satisfactory distance between the eddy current probe 56 and the stator 30.

Figure 3:
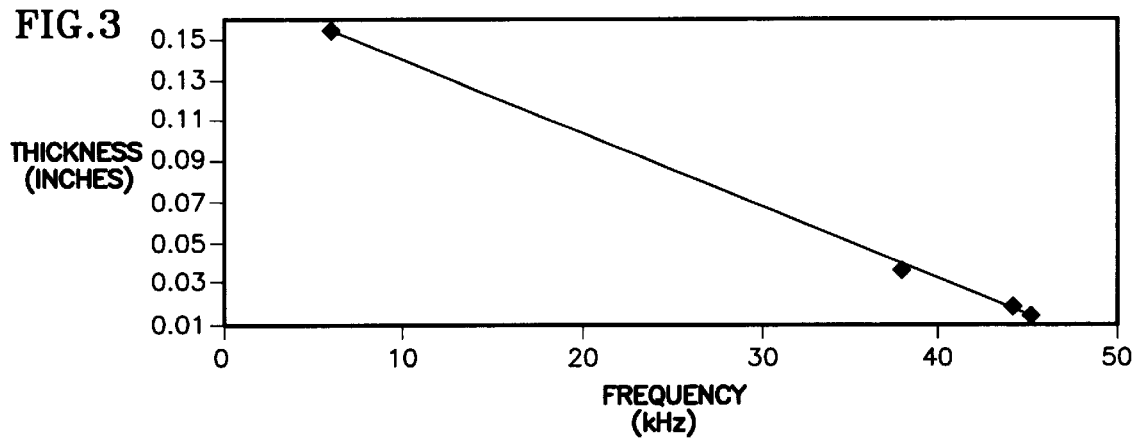
FIG. 3 is a calibration curve indicating thickness versus rolloff frequency characteristics for use with the system of FIG. 1.
Figure 4:
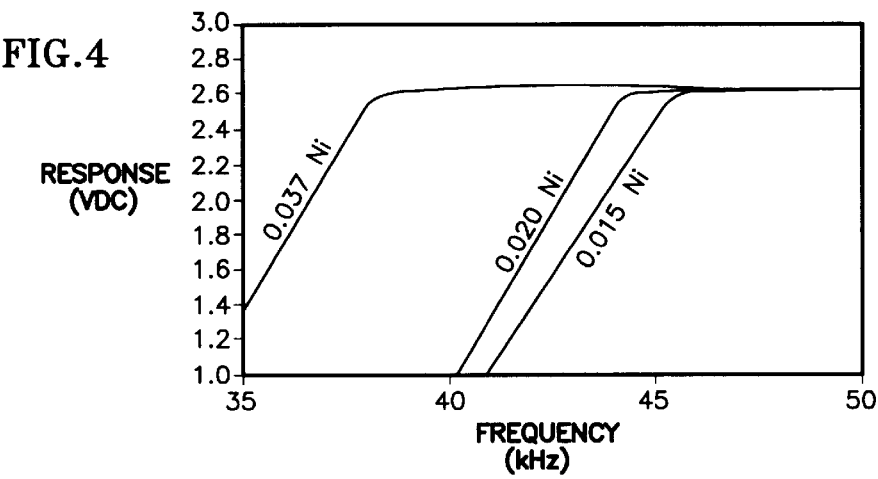
FIG. 4 is a calibration curve indicating seal thickness versus complex impedance rolloff frequency characteristics for use with the system of FIG. 1.

The measurement of the thickness is accomplished by operating the eddy current measurement system at a plurality of drive signal frequencies and obtaining a data signal indicative of the impedance at each frequency. In doing so, the drive frequency may be incrementally decreased, which incrementally increases the depth of penetration of the electromagnetic field and the eddy currents. The impedances are in turn used to determine a rolloff frequency, i.e., a frequency at which the impedance undergoes a significant drop. The rolloff frequency corresponds to the frequency at which the induced eddy currents interact with the highly dense, highly conductive stator substrate and thus can be used to detect the seal to stator substrate interface. Various methods may be used to determine the rolloff frequency, including a linear or logarithmically spaced measurement series, or through the application of a search algorithm to detect the rolloff frequency using relatively few readings. The determination of the rolloff frequency is typically based on the resistive component of the impedance, however, the reactive component or the overall impedance could alternatively be used. From FIG. 3, it can be seen that the rolloff frequency is inversely related to the thickness of the material. The thickness is determined on the basis of the rolloff frequency in combination with a calibration formula or a data table indicative of a calibration curve. FIG. 4 has three calibration curves that indicate electrical voltage from the eddy current signal processor as a function of drive signal frequency.

Figure 5:
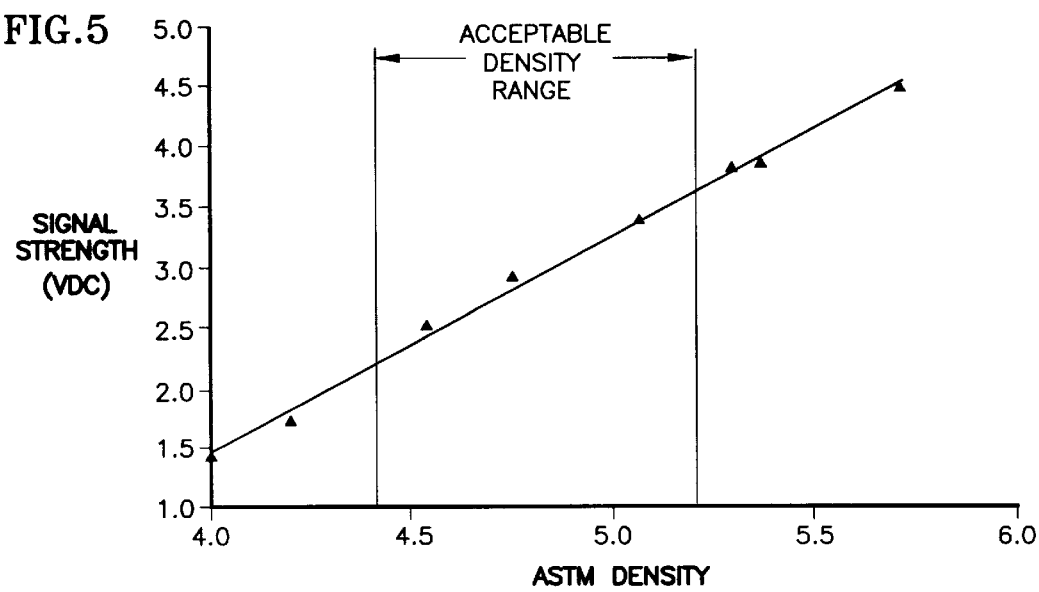
FIG. 5 is a calibration curve indicating seal density versus complex impedance characteristics for use with the system of FIG. 1.

The measurement of the seal density is accomplished by operating the eddy current measurement system with a drive signal frequency preferably below four MHz, for example one MHz. A low end of the drive signal frequency will depend on the thickness of the abradable seal 20. At these frequencies the electromagnetic field and the induced eddy currents penetrate the seal to a significant depth. The response of the eddy current measurement system is a function of both the probe to seal distance and seal density. The density is determined on the basis of the resulting impedance in combination with a calibration formula or a data table indicative of a calibration curve. FIG. 5 has a calibration curve that indicates electrical voltage from the eddy current signal processor as a function of density.

The measurement system 50 may be used to make the above described measurements throughout the fabrication process. Accordingly, density measurements may be generated for various points in the thickness of the abradable seal 20, thereby making it possible to generate a density versus thickness profile. Such a profile may be useful because the abradable seal 20 does not undergo a consolidation such as that employed in powdered metallurgy. Rather, in regard to the abradable seal 20, it is desirable to have distributed, controlled pockets of non metal material so as to achieve the desired characteristics of abradability.

The measured thickness and the measured density of the seal may be used in a feedback control loop for the process. Corrective action, such as modifications to powder flow, carrier gas flow, arc power or plasma gas flow may be applied on the basis of the measured value of seal density. The measured seal thickness can be used to determine the ending point of the thermal spray process.

Although disclosed with respect to a best mode embodiment in which the stator is rotated relative to the spray system and the eddy current probe, this is not required. For example, in an alternative embodiment, the spray system and the eddy current probe are rotated relative to the stator.

The measurement system 50 must be calibrated in order to determine the probe to seal distance, the thickness and the density. Calibration for thickness and density may be accomplished by providing a series of freebody seal specimens (i.e. no substrate) of known thickness and density, and by obtaining a plurality of measurements from the eddy current measurement system for the specimens. A relationship between the measurements and each property may be determined and entered into the supervisory controller 74 for use in measurement of properties of seals of unknown thickness and density. The calibration is preferably performed in advance of such use. Calibration for probe to seal distance is accomplished by measuring the above set of specimens at a variety of probe to seal distances.

While disclosed with respect to an in process inspection, the eddy current techniques disclosed herein may also be applied as a post-process quality control technique. The coating density and thickness can be determined at many locations on the coating. The density can be determined as a function of coating thickness to detect large voids, discontinuities and delamination. Furthermore, different drive signal frequencies result in density measurement for different portions of the thickness of the abradable seal 20. Moreover, by performing the density measurements at a plurality of drive signal frequencies, it is possible to determine the density at a plurality of points in the thickness of the abradable seal 20 and thereby generate a density versus thickness profile. As stated above, such a profile may be useful because the abradable seal 20 does not undergo a consolidation such as that employed in powdered metallurgy, but rather has distributed, controlled pockets of non metal material so as to achieve the desired characteristics of abradability.

As stated above, the density provides an indication of the abradability and the erosion resistance of the seal. However, the eddy current measurements are not limited to use in determining the density of the seal. Rather the measurements may be correlated to any of various properties which may be indicative of at least one of abradability and erosion resistance including but not limited to the abradability, the erosion resistance, the density, the volume fraction of conductive material (metal), the ratio of metal to non metal, the hardness, the conductivity, the resistivity, the magnetic character.

The abradable seal 20 can be a composite (more than one material) or a homogenous material, and can be solid or porous. The material(s) and their conductivity are typically known. If the seal comprises two materials, one is typically a metal and other is typically a non metal or a metal having much lower conductivity.

Although disclosed with respect to a best mode embodiment for use in fabricating and/or inspection of an abradable seal 20 it should be recognized that the invention will be useful in the fabrication and characterization of other coatings as well.

Furthermore, although disclosed hereinabove with respect to coatings having metal volume fractions of no greater than 0.5, it should be clear that the present invention would work for coatings having metal volume fractions higher than 0.5, including but not limited to those having metal volume fractions of about 0.5 (i.e., up to 0.55), those having metal volume fractions in the range between 0.5 and 0.6, those having metal volume fractions in the range between 0.5 and 0.7, and those having metal volume fractions in the range between 0.5 and 0.8.

Although the present invention has been described with reference to a best mode embodiment, this description is not meant to be construed in a limiting sense. Various modifications of the best mode embodiment, as well as additional embodiments of the invention, will be apparent to persons skilled in the art upon reference to this description, without departing from the spirit of the invention, as recited in the claims appended hereto. It is therefore contemplated that the appended claims will cover any such modifications or embodiments as fall within the true scope of the invention.

What is claimed is:

1. A method for inspecting a non homogenous coating comprised of a metal material and another material of at least one type selected from the group consisting of a non metal material, a gas and mixtures thereof, the coating having a metal volume fraction of no greater than 0.5, the method comprising the step of:

using multifrequency eddy current techniques to directly determine density of the coating based on electrical properties of the coating.

2. The method of claim 1 wherein the step of using eddy current techniques includes the steps of:

generating an eddy current in the coating, generating a measurement signal as a function of the eddy current, and determining in response thereto, a measure of the density of the coating.

3. The method of claim 1 wherein the density has been correlated to performance of the coating.

4. The method of claim 1 wherein the coating has a metal volume fraction in the range of from 0.3 to 0.5.

5. The method of claim 1 wherein the other material comprises non metal material.

6. The method of claim 1 wherein the step of using eddy current technique comprises a step of determining a probe to coating distance using a frequency in a range of from one megahertz to ten megahertz.

7. The method of claim 1 wherein the step of using eddy current technique comprises a step of determining a property that is indicative of at least one of abradability and erosion resistance.

8. The method of claim 1 wherein the coating has a metal volume fraction in the range of from 0.3 to 0.5, and the other material comprises non metal material.

9. A method of fabricating an annular component having a coating with a metal volume fraction of no greater than 0.5 thereon and for measuring at least one physical property of the coating, comprising the steps of:

rotating the component relative to a sprayed stream of metal particles and other material having low conductivity relative to that of the metal particles, wherein the metal particles and the other material are deposited onto the surface of the component; and directly determining density of the coating using multifrequency eddy current techniques as the particles and the other material are being deposited onto the surface of the compound.

10. The method of claim 9 wherein the density has been correlated to performance of the coating.

11. The method of claim 9 wherein the coating has a metal volume fraction in the range of from 0.3 to 0.5.

12. The method of claim 9 wherein the other material comprises non metal particles.

13. The method of claim 9 wherein the step of determining density includes the steps of generating an eddy current in the coating, generating a measurement signal as a function of the eddy current, and determining in response thereto, a measure of the density of the coating.

14. The method of claim 9 wherein the step of determining density comprises a step of determining a probe to coating distance using a frequency in a range of from one megahertz to ten megahertz.

15. The method of claim 9 wherein the step of determining density comprises a step of determining a thickness of the coating by making a plurality of eddy current measurements over a range of frequencies.

16. The method of claim 9 wherein the step of determining density comprises a step of determining a property that is indicative of at least one of abradability and erosion resistance.

17. The method of claims 16 wherein the coating has a metal volume fraction in the range of from 0.3 to 0.5, and the other material comprises non metal particles.

18. The method of claim 9 further wherein the step of determining is performed while the particles are deposited .

19. The method of claim 9 further comprising the step of adjusting the ratio of the particles in the sprayed stream as a function of the at least one physical property of the coating.

20. A method of fabricating an annular component having a coating with a metal volume fraction of no greater than 0.5 thereon and for measuring at least one physical property of the coating, comprising the steps of:

rotating the component relative to a sprayed stream of metal particles and other material having low conductivity relative to that of the metal particles, wherein the metal particles and the other material are deposited onto the surface of the component; and using eddy current techniques as the coating is deposited to determine density of the coating indicative of at least one of erosion resistance and abradability of the coating at a plurality of points in a thickness of the coating.

21. A method for inspecting a non homogenous coating comprised of a metal material and another material of at least one type selected from the group consisting of a non metal material, a gas and mixtures thereof, the coating having a metal volume fraction of no greater than 0.5, the method comprising the step of:

using eddy current techniques to determine thickness of the coating based on a rolloff frequency.

22. The method of claim 21 wherein the rolloff frequency is a frequency at which impedance undergoes a significant drop.

23. A method of fabricating an annular component having a coating with a metal volume fraction of no greater than 0.5 thereon and for measuring at least one physical property of the coating, comprising the steps of:

rotating the component relative to a sprayed stream of metal particles and other material having low conductivity relative to that of the metal particles, wherein the metal particles and the other material are deposited onto the surface of the component; and determining thickness of the coating using eddy current techniques based on rolloff frequency.

24. The method of claim 23 wherein the rolloff frequency is frequency at which impedance under goes a significant drop.

* * * * *